United States Patent
Badger et al.

(10) Patent No.: US 7,443,497 B2
(45) Date of Patent: Oct. 28, 2008

(54) MASK INSPECTION DNIR PLACEMENT BASED ON LOCATION OF TRI-TONE LEVEL DATABASE IMAGES (2P SHAPES)

(75) Inventors: Karen D. Badger, Milton, VT (US); David L. Katcoff, Jericho, VT (US); Jeffrey P. Lissor, Plainfield, VT (US); Christopher K. Magg, Jericho, VT (US)

(73) Assignee: International Business Machines Corporation, Armonk, NY (US)

( * ) Notice: Subject to any disclaimer, the term of this patent is extended or adjusted under 35 U.S.C. 154(b) by 283 days.

(21) Appl. No.: 11/162,179

(22) Filed: Aug. 31, 2005

(65) Prior Publication Data

US 2007/0050163 A1    Mar. 1, 2007

(51) Int. Cl.
*G01N 21/00* (2006.01)
(52) U.S. Cl. .................................................. 356/237.4
(58) Field of Classification Search .... 356/237.4–237.5
See application file for complete search history.

(56) References Cited

U.S. PATENT DOCUMENTS

| | | | |
|---|---|---|---|
| 4,896,278 A * | 1/1990 | Grove ........................ | 702/36 |
| 5,748,317 A * | 5/1998 | Maris et al. ................. | 356/502 |
| 5,807,649 A | 9/1998 | Liebmann et al. | |
| 6,327,379 B2 | 12/2001 | Matsuyama et al. | |
| 6,526,164 B1 * | 2/2003 | Mansfield et al. ............ | 382/144 |
| 6,654,488 B1 | 11/2003 | Behun et al. | |
| 6,797,438 B1 | 9/2004 | Lukanc et al. | |
| 6,977,183 B1 * | 12/2005 | DiBiase ........................ | 438/7 |
| 2003/0228050 A1 | 12/2003 | Geshel et al. | |

* cited by examiner

*Primary Examiner*—Tarifur R. Chowdhury
*Assistant Examiner*—Isiaka O Akanbi
(74) *Attorney, Agent, or Firm*—Delio & Peterson, LLC; Kelly M. Nowak; Richard Kotulak

(57) ABSTRACT

Methods, systems, program storage devices and computer program products for mask inspection that automate the detection and placement of do not inspect regions ("DNIR") for intentionally induced defects on masks. A location of an intentional defect is identified on a mask, and then logic relating to this location is translated into a shape that represents a DNIR for the intentional defect. A second shape representing another DNIR of the mask is provided. It is then determined if the first and second shapes for DNIRs violate a processing rule of the inspection tool, and if so, the violated rule is corrected for by generating a single contiguous DNIR by overlapping the first and second shapes. The inspection tool then utilizes the first and second shapes representing DNIRs, along with any single contiguous DNIRs, to inspect the mask for unintentional defects while avoiding intentional defects.

27 Claims, 2 Drawing Sheets

MASK INSPECTION DNIR PLACEMENT BASED ON LOCATION OF TRI-TONE LEVEL DATABASE IMAGES (2P SHAPES)

BACKGROUND OF THE INVENTION

1. Field of the Invention

The present invention is directed to the manufacture of masks used in the lithographic production of integrated circuits and, in particular, to the inspection and detection of metallized defects on patterned masks.

2. Description of Related Art

The manufacture of semiconductor substrates such as wafers and chips involve the use of high-resolution lithography systems. In such systems, a patterned mask (i.e., reticle) is illuminated with radiation (e.g., laser radiation or radiation from an arc lamp) that passes through the illumination system and achieves a high-degree of illumination uniformity over the illuminated portion of the mask.

FIG. 1 shows a typical prior art mask 80 with a device exposure region 82 having a square or rectangular shape positioned at the center of the mask and an opaque region 84. The device exposure region includes transparent portions that may be made of glass, quartz, or the like, and opaque portions commonly made of chrome for defining a device pattern 88 (which is not illustrated in detail in the figure). As an alternative, phase shifting masks (PSMs) have also been employed in order to increase the resolution of the critical active area patterns projected on the mask. The increased resolution of PSMs enables smaller line widths and tighter pitches to be exposed on the resist and consequently etched into or deposited on the wafer substrate.

Also within the mask is a kerf region 86, or discardable portion of the semiconductor wafer, that resides at the periphery of the device region 82 and contains important information regarding the photolithographic process of the wafer and usually includes test structures to verify the performance of the photolithographic process. Illumination from a light source is allowed to travel through the transparent portions in the device exposure region, while the opaque regions block the light such that light does not reach the wafer.

Since an ongoing concern in semiconductor technology is the maximization of manufacturing yield, it has become conventional to fabricate intentionally induced defect test structures (i.e., 2P ("phase shift") level shapes) isolated from the production circuits that serve to yield reliability data on the regular product circuits. The principal reason for fabricating these defect test structures is that the integrated circuits themselves cannot be probed because the interconnections in the device are neither accessible electrically nor can the regions be isolated from one another to provide accurate data.

The intentionally induced defect structures are commonly formed in the kerf region of the mask and comprise metallized structures, typically made of chrome. As such, when imaging the wafer using the mask, the defect structures and the imaging pattern are transferred to the same wafers on which the actual semiconductor devices are fabricated. In so doing, the defect test structures are fabricated in exactly the same processing environment at exactly the same time as the actual semiconductor devices. This allows the intentionally induced defect structures to be more accurately indicative of the processing defects that will occur in the actual products.

However, during the process of inspecting the masks for defects, the intentionally induced defect structures may introduce a significant amount of false and nuisance noise. This is particularly true for those masks having reduced dimensions that must be inspected at reduced sensitivities.

Conventional approaches aimed at avoiding detection of intentionally induced defect test structures have been to reduce the sensitivity at which the inspection tool is run. However, it has been found that by running inspection tools at reduced sensitivities, processing-induced defects residing on the mask may not be detected by the inspection tool, especially for masks with reduced sizes. If not detected, these defects can ultimately lead to product failure. Another approach has been to manually inspect the mask for intentionally induced defects, and to designate any located intentionally induced defects as do not inspect regions (i.e., those regions of the mask that the inspection tool will not inspect). Yet this approach is undesirably tedious, time consuming and often prone to mistakes, either by missing some intentionally induced defects and/or by misplacement of the do not inspect regions.

As such, due to current semiconductor devices having reduced dimensions, and with future generations that will have even smaller dimensions, a need exists in the art for providing improved methods, systems, articles and program products for the detection of metal defects on patterned masks.

SUMMARY OF THE INVENTION

Bearing in mind the problems and deficiencies of the prior art, it is therefore an object of the present invention to provide improved methods, systems, articles and program products for inspecting and detecting metallized defects on patterned masks.

It is another object of the present invention to provide improved methods, systems, articles and program products that allow inspection tools to run at increased sensitivity for inspecting and detecting metallized defects on patterned masks.

A further object of the invention is to provide improved methods, systems, articles and program products that reduce the amount of false and nuisance noise that is detected by the inspection tool during the inspection of patterned masks for defects Still another object of the present invention is to provide improved methods, systems, articles and program products that automatically, easily and efficiently detect and locate metallized defects on patterned masks.

Still other objects and advantages of the invention will in part be obvious and will in part be apparent from the specification.

The above and other objects, which will be apparent to those skilled in the art, are achieved in the present invention, which is directed to a method of mask inspection. The method includes identifying a location of an intentionally induced defect on a mask, and then converting this location to a first shape that represents a first do not inspect region of the mask. A second shape that represents a second do not inspect region of the mask is provided, and the mask is then inspected. During this mask inspection, the first and second shapes that represent do not inspect regions are used such that the inspection tool is able to detect unintentional defects on the mask, while avoiding the intentionally induced defects and predefined do not inspect regions on the mask.

In this aspect, the second do not inspect region may be a predefined do not inspect region or a second location of another intentionally induced defect on the mask. The first shape representing the intentionally induced defect may be a metal defect, such as a chrome defect, which may reside in the kerf region of the mask, the device region of the mask, or even combinations thereof. The mask may be a phase shift mask.

The first and second shapes are determined using an analysis component such as, for example, an inspection tool or an external processor. These first and second shapes comprise geometrical shapes of a sufficient size and shape to entirely cover the first and second do not inspect regions during the inspection of the mask. In so doing, the shapes may be regular finite shapes, irregular finite shapes, rectangles, squares, circles, and combinations thereof. Preferably, the first shape is validated to ensure that it entirely covers the location of the intentionally induced defect on the mask prior to inspection.

Further in this aspect, the method may further include providing write data, and extracting intentionally induced defect data along with predefined do not inspect region data from the write data. The method may also include determining if the first and second shapes that represent do not inspect regions violate a processing rule of the inspection tool. If it is determined that these first and second shapes violate a processing rule, a single contiguous do not inspect region is generated in accordance with the invention by overlapping the first and second finite shapes. The mask may then be inspected by also using these single contiguous do not inspect regions in combination with any first and second shapes that do not violate processing rules of the tool.

Alternatively, the method may further include identifying a plurality of locations of intentionally induced defects on the mask. In this aspect, these locations are converted into a first set of shapes that represent do not inspect regions for the intentionally induced defects. Also provided is a second set of shapes that represent predefined do not inspect regions of the mask. The method then identifies any adjacent shapes within the first and second sets of shapes, and determines if these adjacent shapes representing do not inspect regions violate any processing rules of the inspection tool. Any detected violated rules are then corrected for by modifying at least one of the adjacent shapes, and then the mask is inspected using the first and second sets of shapes, along with any of the modified shapes, that represent do not inspect regions on the mask such that the inspection tool detects the unintentional defects on the mask.

The step of correcting for any of the violated processing rules includes generating a single contiguous do not inspect region by overlapping adjacent shapes that violate processing rules. These adjacent shapes may be adjacent shapes each for intentionally induced defects, adjacent shapes each for predefined do not inspect regions, or even combinations thereof. Preferably, a distance between the two adjacent shapes is determined, and if this distance violates the processing rules of the tool, then the smaller of the compared adjacent shapes is expanded to overlap the larger of the compared adjacent shapes. In so doing, this smaller shape may represent a do not inspect region for an intentionally induced defect or it may represent a predefined do not inspect region.

In another aspect, the invention may be directed to a system for mask inspection. The system includes a mask containing intentionally induced defects, write data, an analysis component, software running on the analysis component and an inspection tool. The write data includes identifications of first locations for intentionally induced defects on the mask, and second locations for predefined do not inspect regions on the mask. An essential feature of the system is that the software translates the first locations into a first set of logic for finite shapes that represent do not inspect regions for the intentionally induced defects, and translates the second locations into a second set of logic for finite shapes representing predefined do not inspect regions. The software then determines if these first and second sets of logic violate a processing rule of the inspection tool, and if they do, then the software generates a single contiguous do not inspect region by overlapping selected logic from the first and second sets of logic. The inspection tool then uses this first and second sets of logic, along with any single contiguous do not inspect regions, to inspect the mask for unintentional defects while avoiding the intentionally induced defects and the predefined do not inspect regions.

In still other aspects, the invention is directed to program storage devices and computer program products for performing and for causing a computer to perform and execute the above described method steps of the invention.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

Figure 1:
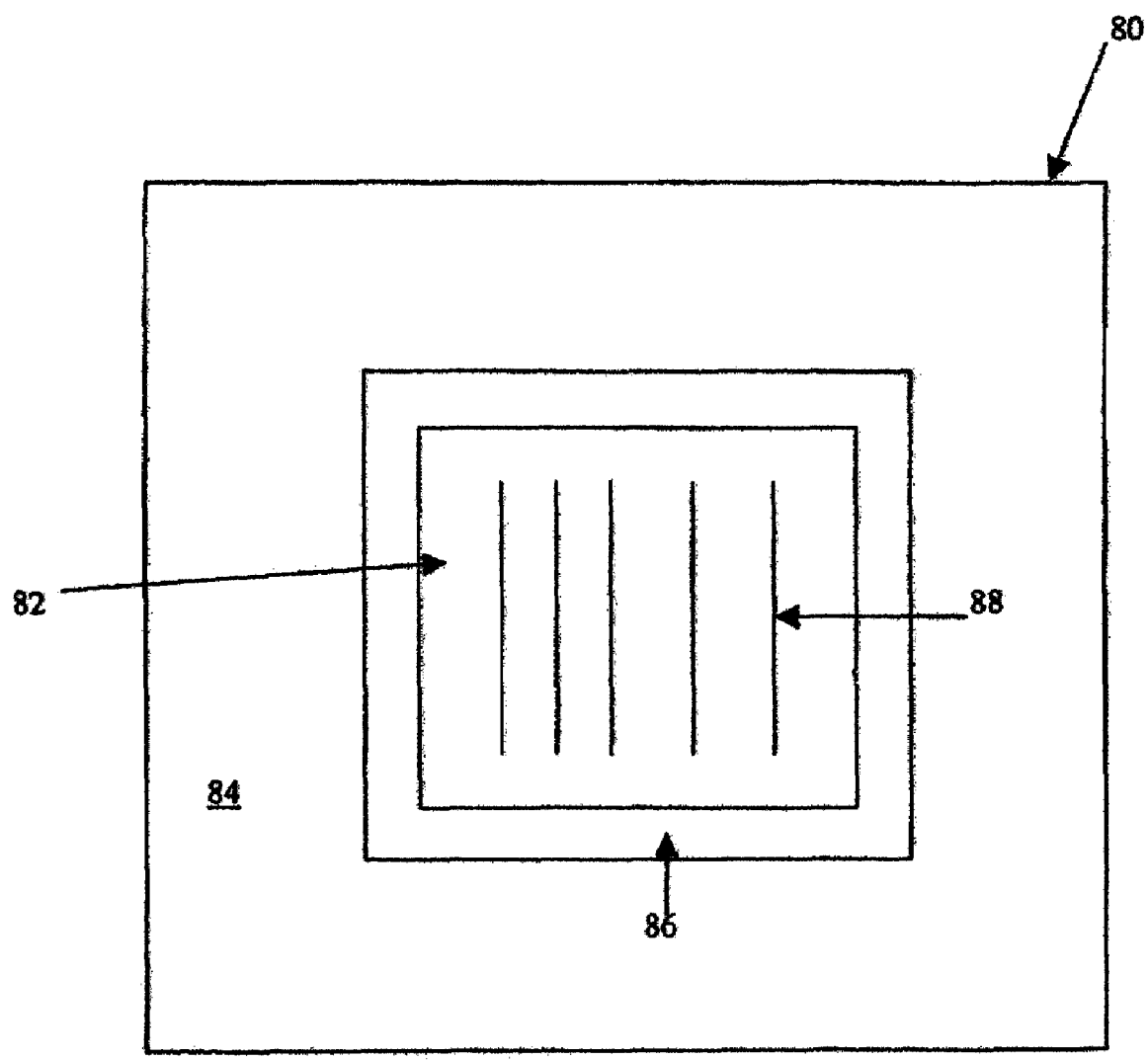
FIG. 1 illustrates a conventional prior art mask (i.e., reticle) used in semiconductor wafer fabrication.

In describing the preferred embodiment of the present invention, reference will be made herein to FIGS. 1-2 of the drawings in which like numerals refer to like features of the invention.

The present invention is directed to inspecting and detecting defects, particularly metal defects, on patterned masks. In the fabrication of semiconductor devices, particularly those having reduced dimensions, the formation of intentionally induced defect test structures undesirably generates a significant amount of false and nuisance noise. These intentionally induced defect test structures are commonly formed of chrome in the kerf region of the mask.

In the process of forming these intentionally induced defect test structures on a mask, predetermined specifications relating to the fabrication of such test structures are written to a processing tool for forming the structures. These predetermined specifications include write data (i.e. 2P level data) that identifies the size, shape and location of the intentional defect test structures to be fabricated on the mask. After the test structures and the desired design pattern are formed on the mask, the mask is scanned for any undesirable defects caused during processing. These undesirable defects may include unintentionally induced defects in the kerf region, the device region, or even combinations thereof.

However, as device and mask dimensions continue to shrink, it is particularly difficult for the inspection tools to detect intentionally induced defect test structures. This is particularly true for test structures formed on phase shifting masks (PSMs), which allow for an increase in the resolution of the critical active area patterns projected on the mask.

Since it is desirable to easily, quickly and efficiently detect any undesirable defects on the mask, it is advantageous to know where the intentionally induced defect test structures reside on the mask prior to mask inspection. The present invention provides methods, systems, articles and program products that automatically identify and designate intentionally induced defect test structures prior to inspecting the mask.

Figure 2:
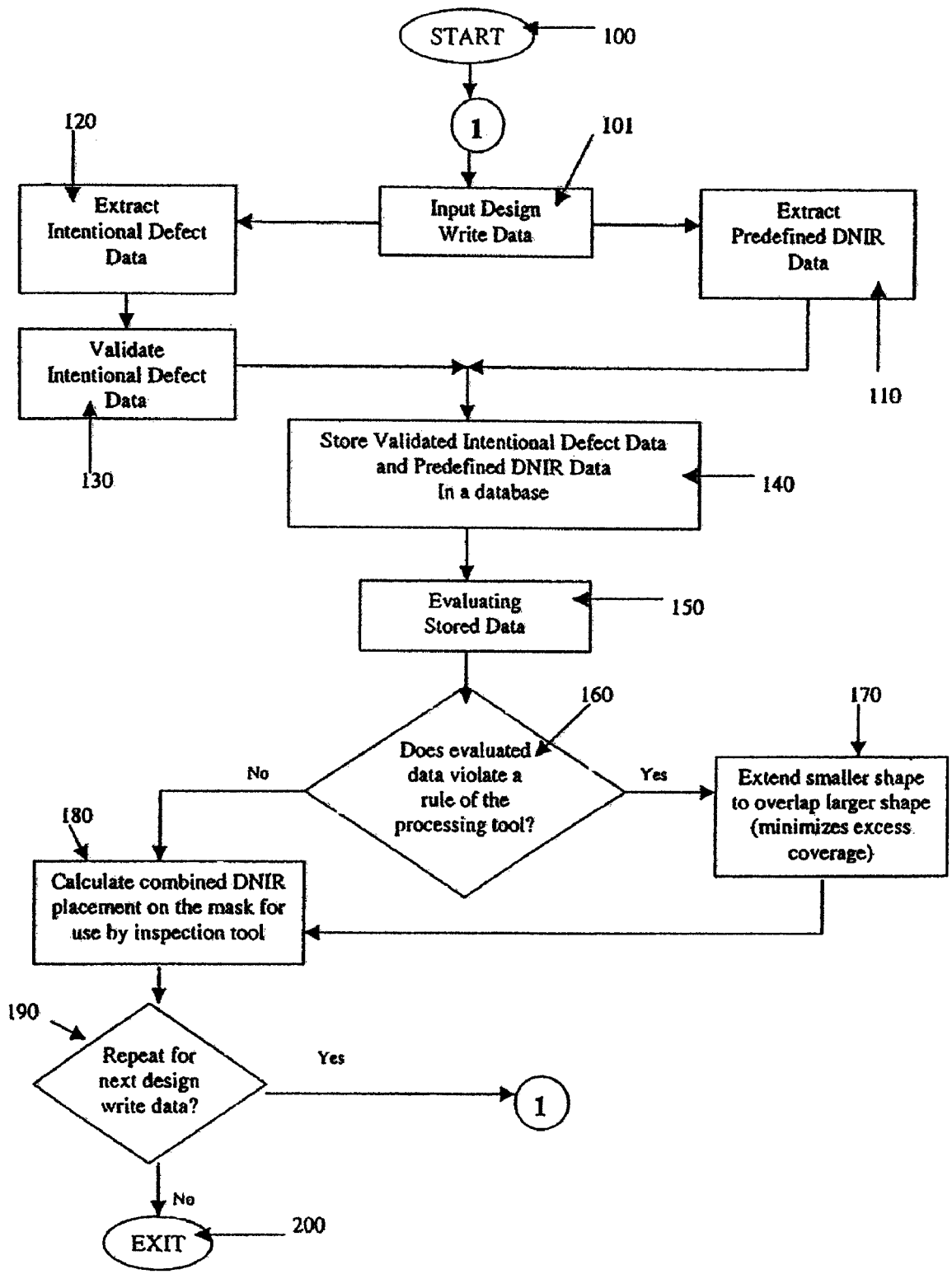
FIG. 2 illustrates a process flow for inspecting and detecting residual chrome defects on patterned masks in accordance with the invention.

Referring now to the invention, FIG. 2 shows a preferred process flow whereby the process is started (step 100) and then write data is first provided for the specific design of the mask. The write data includes predetermined design data for the desired patterns and tests structures, which may include design data for multiple layers for building the mask. Using this write data, the mask is fabricated to include various layers that include transparent regions, design patterns, test structures, and the like. The fabricated mask is then inspected for any undesirable defects.

The write data correlating to the mask being inspected is input into an analysis component (step 101). This write data includes the predetermined design data for the desired patterns, as well as the identification of the sizes, shapes and locations of all intentionally induced defect test structures formed on the mask. It should be appreciated that the input write data may need to be converted into a format readable by the analysis component. For instance, wherein the present invention is initiated using a korn shell script in AIX running in C language, the write data may need to be converted to readable clib formatted data.

In accordance with the invention, the analysis component may be an inspection tool used for inspecting and detecting any defects on the mask that contains appropriate software, or alternatively, an external processor in communication with the inspection tool, such as a computer. For instance, the inspection tool may comprise any known defect control tool used in the semiconductor technology industry such as, for example, a KLA-SLF or KLA-5XX tool made by KLA-Tencor Corporation, San Jose, Calif.

In continuing the process flow, the design data and test structure data are extracted from the write data using the analysis component. This extracted design data is then examined for any predefined do not inspect regions (hereinafter referred to as predefined "DNIRs") embedded within the design data (step 110). Commonly, these predefined DNIRs are defined within the design data upstream of the present process flow. The extracted design data is also examined for extraction of any data relating to the fabrication of intentionally induced defect test structures. Once extracted, this test structure data is analyzed to identify the sizes, shapes and locations of all intentionally induced defect test structures that should be residing on the mask after mask fabrication (step 120).

Using the analyzed test structure data, each location on the mask where an intentionally induced defect test structure is to be fabricated is converted into a do not inspect region (hereinafter referred to as a test structure "DNIR"). Generally, these locations where fabricated intentionally induced test structures are to be formed are in the kerf region, however, some test structures, or portions thereof, may be formed in the device region due to processing errors. In so doing, the logic of the invention translates the locations where defect test structures are to be formed into finite geometrical shapes that represent test structure DNIRs. That is, these test structure DNIRs are locations that will not be inspected downstream during the mask inspection steps.

Each finite geometrical shape is determined by calculating the limits of its vertices in relation to their distances substantially from a predefined center point of where the intentionally induced defect test structure should be formed on the mask in accordance with the design write data. An essential feature is that each finite geometrical shape must be of a sufficient size and shape to substantially cover the entire size and shape of the locations of the identified intentionally induced test structure. For instance, the finite geometrical shapes may be regular or irregular shapes of squares, rectangles, circles, and the like, or even combinations thereof. In the preferred embodiment the finite geometrical shapes are rectangular.

Also converted into finite geometrical shapes are the predefined DNIRs that have been defined upstream of the present process flow. These shapes representing predefined DNIRs are generally formed in the device region.

The finite geometrical shapes representing test structure DNIRs, for locations where intentionally induced defect test structures are to be fabricated on the mask, are then validated (step 130). This is accomplished by expanding the finite geometrical shapes. In so doing, the dimensions of the finite geometrical shapes are expanded within the logic of the system just enough to ensure that the inspection tool will be able to inspect the shapes in accordance with the processing rules of the tool. This expansion is also advantageous for ensuring that the extended shapes representing test structure DNIRs sufficiently cover all locations where it is believed that such test structures will reside on the mask, which is particularly useful in the event of misplacement of a test structure(s) during processing. For instance, the finite shape may be expanded by about 0.75 microns using a 1× optical inspection tool.

A first data set relating to the finite shapes that represent test structure DNIRs is then added to a database, along with a second data set relating to the finite shapes that represent predefined DNIRs (step 140). These first and second data sets of finite shapes representing DNIRs are combined together within the database, and then this data is evaluated as a single unit (step 150).

In evaluating the stored data, data relating to the first and second data sets are compared against each other. This comparison step determines the proximity of each finite shape representing a DNIR with respect to adjacent finite shapes. That is, finite shapes representing test structure DNIRs are compared against each other, finite shapes for test structure DNIRs are compared against those shapes of predefined DNIRs, and finite shapes representing predefined DNIRs are compared against each other. In the preferred embodiment, it is finite shapes representing test structure DNIRs that are compared against either other, adjacent test structure DNIRs or predefined DNIRs.

In accordance with the invention, the finite shapes representing DNIRs are compared against one another to ensure that all shapes meet the processing requirements and rules of the inspection tool on which the mask is to be analyzed (step 160). In performing these comparisons, the proximity in distance of a first shape representing a DNIR is determined with respect to a second shape representing an adjacent DNIR. This proximity distance step includes determining whether adjacent shapes overlap each other, reside above or under one another, or even to the right or left of each other. In the invention, the proximity distances may be measured in terms of inspection-resolution, microns per pixel, and the like, depending upon the units and measures capabilities of the inspection tool.

It is then determined whether or not adjacent DNIR shapes are too close to one another using these determined proximity distances. In the preferred embodiment, it is determined whether or not any test structure DNIR is too close to an adjacent DNIR shape, whether this other DNIR shape comprises a test structure DNIR or a predefined DNIR. If it is determined that the two compared DNIR shapes are too close to one another, particularly, that the test structure DNIR is too close to an adjacent DNIR shape, then the smaller of these DNIR shapes is modified (step 170). This modification of the smaller DNIR shapes significantly avoids any spacing and/or sizing violations that would interrupt running of the inspection tool, thereby allowing the mask to be inspected easily and efficiently without interruption.

In modifying the shapes representing DNIRs, the shorter of two DNIR shapes is preferably modified. This modified DNIR shape may be either the test structure DNIR or the predefined DNIR. In so doing, a side of the smaller DNIR shape is preferably extended in a direction parallel to a side of the adjacent larger DNIR shape. It is essential that this side of the smaller DNIR shape be extended in the parallel direction just enough to overlap the adjacent larger DNIR shape. For instance, wherein a test structure DNIR is closer than 128/ scale at 1× as compared to an adjacent DNIR shape, the smaller of these two DNIR shapes is extended by about 0.75 microns using a 1×optic inspection tool in the parallel direction, such that this smaller shape now overlaps the larger shape.

As such, when it is determined that two adjacent DNIR shapes are too close to one another such that this spacing violates the requirements and rules of the inspection tool, the two adjacent DNIR shapes are merged together to form a single DNIR region. The process is repeated for all adjacent DNIR shapes residing too close to one another, and those violating the spacing rules of the inspection tool are merged to form DNIR regions. In so doing, it should be appreciated that a DNIR region may be merged with an adjacent DNIR shape. Merged DNIR regions, which meet the requirements and rules of the inspection tool, are saved as vector arrays. This data set of merged DNIR regions are then stored in a database along with those test structure DNIR shapes and predefined DNIR shapes that meet the inspection tool rules.

Placements of the merged DNIR regions, test structure DNIR shapes and predefined DNIR shapes are determined on the mask, and then the inspection tool may inspect the mask using these combined placements (step 180). That is, the inspection tool will not inspect these DNIRs on the mask for defects. Again, those regions of the mask not to be inspected include test structure DNIR shapes that meet the tool rules, predefined DNIR shapes that meet the tool rules, merged DNIR regions, and combinations thereof. It is then determined if the present process is to be repeated for another design write data (step 190). If the process is to be repeated, the process flow repeats back to step 101. Otherwise the process and system are exited (step 200).

A critical feature of the present invention of converting locations where intentionally induced test structures are to be formed on the mask into DNIR shapes, or even DNIR regions, is that it occurs prior to the actual inspection of the mask for any defects. This advantageously allows inspection tools to automatically, easily and efficiently run at increased sensitivity for inspecting and detecting metallized defects on patterned masks, while significantly reducing the amount of false and nuisance noise detected by the inspection tool. The invention also enhances the detection of unintentional defects on the patterned masks during inspection by predefining and knowing the location and placements of the intentionally induced defects on the mask.

The invention is particularly useful for phase shifting masks (PSMs), such as quartz PSMs having chrome and MoSi structures formed thereon. For instance, with the presence of intentionally induced chrome test structures in the kerf areas of this type of quartz PSM, three levels of transparency exist on the mask, particularly, 0% transparency in locations of chrome test structures, either 20% or 54% transparency in locations of MoSi depending on whether the reticle is 248 nm or 193 nm thick, and 100% transparency in locations of quartz. In conventional approaches, the ability to inspect residual chrome defects and intentionally induced chrome defects in the kerf region on 248 nm and 193 nm MoSi PSM masks is extremely poor. As such, once the inspection tool detects a chrome defect, it is even more difficult, and commonly unable, to distinguish the intentionally induced chrome defects from the processing induced unintentional chrome defects. The present invention avoids these problems by locating and identifying the intentionally induced chrome defect locations prior to running the inspection tool, and as such, interruptions in running the inspection tool and the need for manually inspecting the mask for intentional defects are substantially avoided. The invention advantageously allows the inspection tool to inspect PSMs as a non-phase shift type mask.

The method of the present invention for detecting defects on masks may be implemented by a computer program or software incorporating the process steps and instructions described above in otherwise conventional program code, which may be stored on an electronic design automation (EDA) tool or an otherwise conventional program storage device. Computer readable program code means in known source code may be employed to convert the methods described below for use on a computer. The program code, as well as any input information required, may be stored in EDA tool or computer on a program storage device, such as a semiconductor chip, a read-only memory, magnetic media such as a diskette or computer hard drive, or optical media such as a CD or DVD ROM. The system has a microprocessor for reading and executing the program code stored on the device in the manner described above.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A method of mask inspection comprising:
identifying a location of an intentionally induced defect on a mask;
converting said location of said intentionally induced defect to a first finite geometrical shape that represents a first do not inspect region of said mask;
providing a second finite geometrical shape that represents a second do not inspect region of said mask;
validating said first finite geometrical shape to ensure that said first finite geometrical shape entirely covers said location of said intentionally induced defect on said mask prior to inspecting said mask; and
inspecting said mask using said validated first finite geometrical shape and said second finite geometrical shape that each represent do not inspect regions such that an inspection tool is able to detect unintentional defects on said mask while avoiding said intentionally induced defects and said predefined do not inspect regions.

2. The method of claim 1 wherein said second do not inspect region comprises a predefined do not inspect region of said mask.

3. The method of claim 1 wherein said second do not inspect region comprises a second location of a second intentionally induced defect on said mask.

4. The method of claim 1 wherein said first finite geometrical shape that represents said first do not inspect region resides in a region of said mask selected from the group consisting of a kerf region, a device region, and combinations thereof.

5. The method of claim 1 wherein said intentionally induced defect comprises a metal defect.

6. The method of claim 5 wherein said metal defect comprises chrome.

7. The method of claim 1 wherein said mask comprises a phase shift mask.

8. The method of claim 1 wherein said first and second shapes are determined using an analysis component selected from the group consisting of an inspection tool and an external processor.

9. The method of claim 1 wherein said first and second finite geometrical shapes comprise geometrical shapes of a sufficient size and shape to entirely cover said first and second do not inspect regions during said inspection of said mask.

10. The method of claim 4 wherein said geometrical shapes are selected from the group consisting of regular finite shapes, irregular finite shapes, rectangles, squares, circles, and combinations thereof.

11. The method of claim 1 wherein said first finite geometrical shape is validated by expanding at least one dimension of said first finite geometrical shape.

12. The method of claim 1 further including the steps of:
providing write data;
extracting intentionally induced defect data from said write data; and
extracting predefined do not inspect region data from said write data.

13. The method of claim 1 further including the steps of:
determining if said first and second finite geometrical shapes that represent do not inspect regions violate a processing rule of said inspection tool;
if said first and second finite geometrical shapes violate said processing rule, generating a single contiguous do not inspect region by overlapping said first and second finite geometrical shapes; and
inspecting said mask using said single contiguous do not inspect region such that said inspection tool is able to detect unintentional defects on said mask.

14. The method of claim 13 wherein a distance between said first and second finite geometrical shapes is determined, and if said distance violates said processing rule, said method further comprising comparing a size of said first and second finite geometrical shapes against each other, and a smaller of said first and second finite geometrical shapes being modified to overlap at least a portion of a larger of said first and second finite geometrical shapes to generate said single contiguous do not inspect region.

15. The method of claim 1 further including the steps of:
identifying a plurality of locations of intentionally induced defects on said mask;
converting said locations into a first set of shapes that represent do not inspect regions for said intentionally induced defects, said first finite geometrical shape being included within said first set of shapes;
providing a second set of shapes that represent predefined do not inspect regions of said mask, said second finite geometrical shape being included within said second set of shapes;
identifying adjacent shapes within said first and second sets of shapes;
determining if said adjacent shapes representing do not inspect regions violate any processing rules of said inspection tool;
correcting for any violated said processing rules by modifying at least one of said adjacent shapes; and
inspecting said mask using said first and second sets of shapes, along with any said modified shapes, that represent do not inspect regions on said mask such that said inspection tool detects said unintentional defects on said mask.

16. The method of claim 15 wherein said step of correcting for any said violated processing rules comprises generating a single contiguous do not inspect region by overlapping said adjacent shapes, and said method further including the step of inspecting said mask using said first and second sets of shapes along with said single contiguous do not inspect region.

17. The method of claim 15 wherein data corresponding to said first and second sets of shapes are stored within a database as a single group of shapes representing do not inspect regions on said mask.

18. The method of claim 15 wherein said adjacent shapes comprise at least one shape from said first set of shapes representing do not inspect regions for intentionally induced defects and at least another shape from said second set of shapes representing predefined do not inspect regions.

19. The method of claim 15 wherein said adjacent shapes comprise at least two shapes from said first set of shapes representing do not inspect regions for intentionally induced defects.

20. The method of claim 15 wherein said adjacent shapes comprise at least two shapes from said second set of shapes representing predefined do not inspect regions.

21. The method of claim 15 wherein said step of determining if said adjacent shapes representing do not inspect regions violate any processing rules of said inspection tool comprises determining a distance between said adjacent shapes, and wherein said distance between said adjacent shapes violates said processing rules of said inspection tool, expanding at least one of said adjacent shapes to correct for said violated processing rules.

22. The method of claim 21 wherein said expanded at least one of said adjacent shapes comprises said first finite geometrical shape representing said do not inspect region for said intentionally induced defect.

23. The method of claim 21 wherein said expanded at least one of said adjacent shapes comprises said second finite geometrical shape representing said predefined do not inspect region.

24. A system for mask inspection comprising:
a mask containing intentionally induced defects;
write data including identifications of first locations for said intentionally induced defects and second locations for predefined do not inspect regions on said mask;
an analysis component;
a software component running on said analysis component that translates said first locations into a first set of logic for finite shapes representing do not inspect regions for said intentionally induced defects, translates said second locations into a second set of logic for finite shapes representing predefined do not inspect regions, determines if said first and second sets of logic violate a processing rule of said inspection tool prior to the actual inspection of the mask for any defects, and if said processing rule is violated, generates a single contiguous do not inspect region by overlapping selected logic from said first and second sets of logic prior to said actual inspection; and an inspection tool that uses said first and second sets of logic, along with any single contiguous do not inspect regions, to inspect said mask for unintentional defects while avoiding said intentionally induced defects and said predefined do not inspect regions.

25. The system of claim 24 wherein said analysis component is selected from the group consisting of said inspection tool and a processor external to said inspection tool.

26. A program storage device readable by a machine, tangibly embodying a program of instructions executable by the machine to perform method steps for mask inspection, said method comprising:

- identifying a location of an intentionally induced defect on a mask;
- converting said location of said intentionally induced defect to a first finite geometrical shape that represents a first do not inspect region of said mask;
- providing a second finite geometrical shape that represents a second do not inspect region of said mask;
- validating said first finite geometrical shape to ensure that said first finite geometrical shape entirely covers said location of said intentionally induced defect on said mask prior to inspecting said mask; and
- inspecting said mask using said validated first finite geometrical shape and said second finite geometrical shape that each represent do not inspect regions such that an inspection tool is able to detect unintentional defects on said mask while avoiding said intentionally induced defects and said predefined do not inspect regions.

27. The program storage device of claim 26 further including program instructions executable by the machine to perform the further method steps for mask inspection comprising:

- determining if said first and second finite geometrical shapes that represent do not inspect regions violate a processing rule of said inspection tool;
- if said first and second finite geometrical shapes violate said processing rule, generating a single contiguous do not inspect region by overlapping said first and second finite geometrical finite shapes; and
- inspecting said mask using said single contiguous do not inspect region such that said inspection tool is able to detect unintentional defects on said mask.

* * * * *